(12) United States Patent
Caron et al.

(10) Patent No.: US 9,194,853 B2
(45) Date of Patent: Nov. 24, 2015

(54) USE OF CYCLIC AZABORONATES AS SENSITIVE MATERIALS IN SENSORS FOR DETECTING THE PRESENCE OF PEROXIDES IN A GASEOUS ENVIRONMENT

(75) Inventors: Thomas Caron, La Riche (FR); Myriam Bouhadid, Joue-les-Tours (FR); Eric Pasquinet, Saint Avertin (FR); Pierre Montmeat, La Riche (FR); Francoise Serein-Spirau, Montpellier (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 154 days.

(21) Appl. No.: 13/880,013

(22) PCT Filed: Oct. 17, 2011

(86) PCT No.: PCT/EP2011/068107
§ 371 (c)(1),
(2), (4) Date: Jun. 10, 2013

(87) PCT Pub. No.: WO2012/052399
PCT Pub. Date: Apr. 26, 2012

(65) Prior Publication Data
US 2013/0260471 A1 Oct. 3, 2013

(30) Foreign Application Priority Data
Oct. 19, 2010 (FR) .................................... 10 58530

(51) Int. Cl.
*G01N 33/00* (2006.01)
*C07F 5/02* (2006.01)
(52) U.S. Cl.
CPC ............ *G01N 33/0027* (2013.01); *C07F 5/025* (2013.01); *Y10T 436/206664* (2015.01)

(58) Field of Classification Search
CPC .......................... G01N 33/0027; G01N 5/025
USPC ................ 436/127, 135; 558/289; 564/10
See application file for complete search history.

(56) References Cited

U.S. PATENT DOCUMENTS 2,934,556 A * 4/1960 Hoffmann et al. ............ 558/289
2,939,877 A 6/1960 Washburn
(Continued)

FOREIGN PATENT DOCUMENTS

EP 1291347 A2 3/2003
GB 877874 A 9/1961
(Continued)

OTHER PUBLICATIONS

Patolsky, F. et al, Analytical Chemistry 1999, 71, 3170-3180.*
Martin, S. P. et al, Biosensors and Bioelectronics 2002, 17, 735-739.*
Miller, E. W. et al, Journal of the american Chemical Society 2005, 127, 16652-16659.*
He, F. et al, Advanced Functional Materials 2006, 16, 91-94.*
Lock, J. P. et al, Thin Solid Films 2009, 517, 3584-3587.*
Zhao, W., Angewandte Chemie, International Edition 2009, 48, 3022-3024.*
Sikora, A. et al, Free Radical Biology & Medicine 2009, 1401-1407.*
Lubczyk, D. et al, Sensors and Actuators B: Chemical 2010, 143, 561-566.*
(Continued)

*Primary Examiner* — Arlen Soderquist
(74) *Attorney, Agent, or Firm* — Hultquist, PLLC; Mary B. Grant

(57) ABSTRACT

The invention concerns the use of cyclic azaboronates as sensitive materials in sensors for the detection of the presence of peroxides, in particular hydrogen peroxide, in a gaseous environment. It further concerns new cyclic azaboronates, as well as sensors comprising these azaboronates as sensitive materials. Applications for the invention include the following: fight against terrorism, monitoring for security purposes of sites in which peroxides or peroxidable compounds are manufactured, stored, and/or used, monitoring of atmospheric pollution, etc.

17 Claims, 4 Drawing Sheets

(56) References Cited

U.S. PATENT DOCUMENTS

| | | | |
|---|---|---|---|
| 2,970,130 A | | 1/1961 | Finestone |
| 3,021,206 A | * | 2/1962 | Groszos et al. ............... 558/289 |
| 3,069,454 A | * | 12/1962 | Wilcockson et al. ......... 558/289 |
| 3,269,853 A | * | 8/1966 | English et al. ................ 106/243 |
| 3,598,757 A | * | 8/1971 | Cyba ............................. 558/289 |
| 4,659,817 A | | 4/1987 | Gallop et al. |
| 5,958,787 A | * | 9/1999 | Schonfeld et al. ............ 436/116 |
| 7,232,545 B2 | * | 6/2007 | Centanni et al. .................. 422/3 |
| 2003/0096995 A1 | | 5/2003 | Scherer et al. |
| 2004/0039233 A1 | | 2/2004 | Scherer et al. |
| 2005/0118209 A1 | | 6/2005 | Jentzsch et al. |
| 2006/0105466 A1 | * | 5/2006 | Centanni et al. ............. 436/135 |
| 2008/0261318 A1 | * | 10/2008 | Akhavan-Tafti et al. ....... 436/92 |
| 2008/0319204 A1 | | 12/2008 | Wu et al. |
| 2009/0317913 A1 | * | 12/2009 | Lock et al. .................... 436/106 |
| 2011/0130534 A1 | | 6/2011 | Besnard et al. |
| 2013/0178655 A1 | | 7/2013 | Pasquinet et al. |
| 2013/0315829 A1 | * | 11/2013 | Chang et al. .................. 436/135 |

FOREIGN PATENT DOCUMENTS

| | | |
|---|---|---|
| WO | 8304255 A1 | 12/1983 |
| WO | 03059312 A2 | 7/2003 |
| WO | 03105860 A1 | 12/2003 |
| WO | 2004041833 A1 | 5/2004 |

OTHER PUBLICATIONS

Zhan, X.-Q. et al, Analytica Chimica Acta 2010, 658, 175-179.*

Quin, C. et al, Tetrahedron 2010, 66, 2384-2389.*

Allen, L., et al., "Studies on Aryl Boronic Acids I: Synthesis of Naphthalene-1,4-diboronic Acid", "Journal of Pharmaceutical Sciences", Mar. 1969, pp. 368-369, vol. 58, No. 3.

Bouillon, A., et al., "Synthesis of novel halopyridinylboronic acids and esters. Part 4: Halopyridin-2-yl-boronic acids and esters are stable, crystalline partners for classical Suzuki cross-coupling", "Tetrahedron", 2003, pp. 10043-10049, vol. 59.

Dale, W., et al., "Substituted Styrenes. VII. The Syntheses and Some Reactions of the Vinylbenzeneboronic Acids", "Journal of Organic Chemistry", Jul. 1962, pp. 2598-2603, vol. 27.

Kalinin, A., et al., "Di(isopropylprenyl)borane: A New Hydroboration Reagent for the Synthesis of Alkyl and Alkenyl Boronic Acids", "Angewandte Chemie", 2003, pp. 3399-3404, vol. 42.

Roy, C., et al., "Stability of boronic esters—Structural effects on the relative rates of transesterification of 2-(phenyl)-1,3,2-dioxaborolane", "Journal of Organometallic Chemistry", Oct. 14, 2006, pp. 784-790, vol. 692.

* cited by examiner

USE OF CYCLIC AZABORONATES AS SENSITIVE MATERIALS IN SENSORS FOR DETECTING THE PRESENCE OF PEROXIDES IN A GASEOUS ENVIRONMENT

CROSS-REFERENCE TO RELATED APPLICATIONS

This application is a U.S. national phase under the provisions of 35 U.S.C. §371 of International Patent Application No. PCT/EP11/68107 filed Oct. 17, 2011, which in turn claims priority of French Patent Application No. 1,058,530 filed Oct. 19, 2010. The disclosures of such international patent application and French priority patent application are hereby incorporated herein by reference in their respective entireties, for all purposes.

TECHNICAL FIELD

This invention concerns the use of cyclic azaboronates as sensitive material in sensors for the detection of the presence of peroxides, in particular hydrogen peroxide, in a gaseous environment.

It further concerns new cyclic azaboronates, as well as sensors comprising these azaboronates as sensitive materials.

Because hydrogen peroxide is a compound from which it is possible to prepare explosives such as triacetone triperoxide (TATP) or hexamethylene diamine triperoxide (HMDT) by hand, as well as a breakdown product of these explosives, the invention applies in particular to the fight against terrorism.

Because peroxides are additionally highly unstable compounds that break down easily, with a certain number of them releasing inflammable vapours, the invention also applies to the monitoring for security purposes of areas in which peroxides or peroxidable compounds, i.e., compounds that initially are not peroxides, but are capable of being transformed into peroxides following autooxidation, also known as peroxidation, are manufactured, stocked, and/or used, as well as the monitoring of atmospheric pollution.

PRIOR ART

Peroxides are chemical compounds comprising one or more —O—O— groups, and thus have significant oxidising power.

Accordingly, they are commonly used as bleaching agents, in particular in the textile industry, to bleach natural fibres such as cotton fibres, and in the paper industry to bleach pulp.

They are also commonly used as initiators, promoters, or catalysts in radical polymerisation processes, and as reticulation or vulcanisation agents in the plastics industry.

In addition, each peroxide has its own specific uses.

Thus, for example, hydrogen peroxide, having the formula $H_2O_2$, also known as oxygenated water, is used as:
  disinfectant;
  steriliser, in particular in the food industry, where, when vaporised at high temperature, it serves to sterilise composite packaging just before the insertion of the food products, and in the medical industry, where it serves to sterilise medical devices that are heat-sensitive, and therefore not able to be sterilised by heat;
  agent for treating household or industrial wastewater; and gaseous effluent treatment agent.

Hydrogen peroxide also happens to be usable for hand-making explosives such as TATP or HMTD, and the breakdown of these explosives results in hydrogen peroxide.

Peroxides also have the specific characteristic of being highly unstable compounds that break down, with a certain number of them releasing inflammable vapours.

Thus, it is highly desirable to have devices capable of reliably, but quickly, detecting the presence of peroxides, in particular when they are present as vapours, whether to eliminate a terrorist threat or to prevent any risk of accident in sites where peroxides or peroxidable compounds are manufactured, stored, and/or used.

For a certain number of years, the development of sensors capable of detecting chemical substances in real time has been progressing. The operation of these sensors is based on the use of a sensitive material, i.e., a material with at least one physical property that is modified in contact with the chemicals in question, connected to a system suited to instantaneously measure any variation of this physical property, thus demonstrating the presence of the chemicals in question.

Chemical sensors have multiple advantages: instantaneous results, the possibility of miniaturisation, and, thus, portability, manageability, and substantial independence, low manufacturing and use costs, etc.

Obviously, however, their performance is extremely variable depending on the nature of the sensitive material used.

The objective of the inventors was thus to find compounds capable of reacting to the presence of peroxides in vapour state.

An additional objective is for these compounds to react very rapidly to its presence.

An additional objective was for these compounds to be usable in the form of thin films so as to be able to be used in small sensors that are easily transported and can be used on sites of all kinds.

Yet another objective was for these compounds to be relatively simple to synthesise, and that their synthesis require only reactions classically used in organic chemistry.

In their work, the inventors found that cyclic azaboronates meet all of these requirements, and can thus constitute sensitive materials of choice in sensors for the detection of the presence of these peroxides in a gaseous environment.

DESCRIPTION OF THE INVENTION

Thus, the invention first concerns the use of an azaboronate corresponding to general formula (I) below:

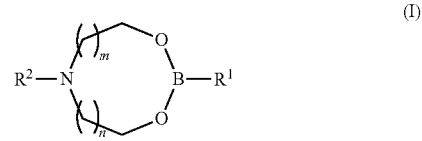

in which:
  m and n independently represent a whole number from 1 to 10;
  $R^1$ represents an aliphatic, cyclic, or partially aliphatic and partially cyclic hydrocarbon group, saturated or unsaturated, comprising 1 to 30 carbon atoms and possibly one or more heteroatoms and/or one or more substituents; whilst
  $R^2$ represents a hydrogen atom, an aliphatic, cyclic, or partially aliphatic and partially cyclic hydrocarbon group, saturated or unsaturated, comprising 1 to 30 carbon atoms and possibly one or more heteroatoms and/or one or more substituents; as a sensitive material in a sensor for the detection of the presence of a peroxide in a gaseous environment by placing the sensor in contact with the gaseous environment.

In general formula (I), the free nitrogen dipole may, depending on the configuration of the azaboronate, fill the electron gap of the boron atom, in which case these nitrogen and boron atoms are bonded to one another by a dative bond.

As noted above, the hydrocarbon groups represented by $R^1$ and $R^2$ may be:

aliphatic, i.e., linear or branched, groups, or cyclic groups, in which case the groups may be mono- or polycyclic, or still partially aliphatic, partially cyclical groups, i.e., groups consisting of at least one linear or branched group bonded covalently to at least one mono- or polycyclic group.

These hydrocarbon groups may additionally be:

saturated groups, i.e., exempt of any —C=C— double or —C≡C— triple bond, or unsaturated groups, in which case the groups may comprise one or more —C=C— double and/or —C≡C— triple bonds.

Additionally, they may comprise one or more heteroatoms, i.e., one or more atoms other than carbon or hydrogen, e.g., one or more oxygen, nitrogen, sulphur, halogen, phosphorus, and/or boron atoms, in which case the heteroatom(s) may just as well form bridges in the hydrocarbon groups or be present in the form of one or more substituents.

They may also be substituted one or more times.

Thus, the hydrocarbon groups represented by $R^1$ and $R^2$ may, in particular, be:

alkyl groups, linear or branched, e.g., methyl, ethyl, n-propyl, i-propyl, n-butyl, i-butyl, s-butyl, t-butyl, n-pentyl, i-pentyl, n-hexyl groups, etc.; or alkenyl or alkynyl groups, linear or branched, e.g., ethenyl or ethynyl, n-propenyl or n-propynyl, i-propenyl or i-propynyl, n-butenyl or n-butynyl, i-butenyl or i-butynyl, s-butenyl or s-butynyl, t-butenyl or t-butynyl, n-pentenyl or n-pentynyl, i-pentenyl or i-pentynyl groups, etc.; or cycloalkyl groups, e.g., cyclopropyl, cyclobutyl, cyclopentyl, cyclohexyl, cycloheptyl groups, etc.; or cycloalkenyl or cycloalkynyl groups, e.g., cyclopentenyl or cyclopentynyl, cyclopentadienyl, cyclohexenyl or cyclohexynyl, cyclohexadienyl groups, etc.; or heterocycloalkyl groups, e.g., dioxolane, dioxane, dithiolane, thioxolane, thioxane, piperazinyl, piperidinyl, pyrrolidinyl, imidazolylidinyl, pyrazolidinyl, tetrahydrofuryl, tetrahydrothienyl, indolinyl, thioazolidinyl groups etc.; or aryl groups, e.g., phenyl, naphthyl, acenaphthyl, pyrenyl, fluorenyl, perylenyl, benzoperylenyl, anthracenyl, fluoranthenyl, pentacenyl, chrysenyl groups, etc.; or heteroaryl groups, e.g., furyl, thienyl, pyrrolyl, oxazolyl, pyrazolyl, thiazolyl, phenothiazolyl, benzothiazolyl, benzofuryl, imidazolyl, benzimidazolyl, triazolyl, pyridyl, pyranyl, quinolinyl, isoquinolinyl, pyrazinyl, pyrimidinyl, carbazolyl, phenothiazolyl, acridinyl, thioxanthenyl, pyridyloxazolyl, benzoxazolyl, benzoxadiazolyl, etc.; or arylalkyl groups (also known as aralkyl groups), i.e., those comprising an alkyl group substituted by an aryl group, e.g., benzyl, phenethyl, carbazolylmethyl, carbazolylethyl, anthracenylmethyl, anthracenylethyl, naphthylmethyl, naphthylethyl groups, etc.; or heteroarylalkyl groups (also known as heteroaralkyl groups), i.e., those comprising an alkyl group substituted with a heteroaryl, e.g., carbazolylmethyl, carbazolylethyl, pyridylmethyl, pyridylethyl, thienylmethyl, thienylethyl, thiazolylmethyl, thiazolylethyl group, etc.; or groups derived from the above groups by one or more substitutions, with the substituent(s) then being preferably chosen from halogen atoms and groups comprising one or more oxygen, nitrogen, sulphur, and/or halogen atoms and a number of carbon atoms from 0 to 10. Such groups are, e.g., —CO, —CN, —COOR', —CHO, —OR', —SR', —SCOR', —SO$_2$R', —NR'R", —CONR'R", —C(Hal)$_3$, —OC(Hal)$_3$, —C(O)Hal, —COOCOR', or phenol groups, in which:

R' represents a hydrogen atom, an alkyl group comprising 1 to 4 carbon atoms, preferably methyl or ethyl, or a phenyl group;

R" represents a hydrogen atom, an alkyl group comprising 1 to 4 carbon atoms, preferably methyl or ethyl, or a phenyl group; whilst Hal represents a halogen atom.

The halogen atoms preferred in the context of the invention are chlorine, fluorine, and bromine atoms.

According to the invention, one of $R^1$ and $R^2$ may be a fluorescent group, i.e., one capable of emitting a luminous signal in response to appropriate luminous excitation.

$C_1$ to $C_{30}$ hydrocarbon groups, as defined above, which are fluorescent, are, e.g., naphthyl, pyrenyl, fluorenyl, carbazolyl, carbazolylmethyl, carbazolylethyl, anthracenyl, anthracenylmethyl, anthracenylethyl, naphthyl, naphthylmethyl, naphthylethyl, toluidinyl, pentacenyl, coumarinyl, perylenyl, benzoperylenyl, fluoranthenyl, benzo[k]fluoranthenyl, phenothiazolyl, benzothiazolyle, imidazolyl, benzimidazolyl, acridinyl, anthraquinyl, thioxanthenyl, fluoresceinyl, rhodaminyl, pyridyloxazolyl, benzoxazolyl, benzoxadiazolyl, and dansyl groups.

In general formula (I), $R^1$ preferably represents an alkyl group comprising 1 to 6 carbon atoms, a heterocycloalkyl group comprising 1 to 3 cycles with 5 or 6 members each, an arylalkyl or heteroarylalkyl group in which the alkyl radical comprises 1 to 6 carbon atoms, and in which the aryl or heteroaryl radical comprises 1 to 3 cycles with 5 or 6 members each, or a group derived therefrom by one or more substitutions as defined above.

Likewise, when $R^2$ represents a hydrocarbon group, it preferably represents an alkyl group comprising 1 to 6 carbon atoms, a heterocycloalkyl group comprising 1 to 3 cycles with 5 or 6 members each, an aryl or heteroaryl group comprising 1 to 3 cycles with 5 or 6 members each, an arylalkyl or heteroarylalkyl group with the alkyl radical comprising 1 to 6 carbon atoms and the aryl or heteroaryl radical comprising 1 to 3 cycles with 5 or 6 members each, or a group derived therefrom by one or more substitutions as defined above.

Furthermore, it is preferred that $R^1$ represents a phenyl group, a phenyl group substituted by one or more halogen atoms, preferably bromine, a benzofuryl group, a phenethyl group, a phenethyl group substituted by a phenoxy group, a pyridyl group, a carbazolylethyl group, a tetrahydrothienyl group, or a tetrahydrothienyl group in which the sulphur atom is bonded to two oxygen atoms (in which case this sulphur atom forms a sulphoxide group with these oxygen atoms), whilst it is preferred that $R^2$ represents a hydrogen atom, an alkyl group comprising 1 to 4 carbon atoms, a phenyl group, a naphthylmethyl group or an anthracenylmethyl group.

Furthermore, it is preferred for m and n to represent, independently, 1 or 2, and even more so for them both to represent 1.

Thus, particularly preferred azaboronates are those corresponding to general formula (I), in which m and n are 1, and in which:
- $R^1$ represents a phenyl group, whilst $R^2$ represents an ethyl group, or
- $R^1$ represents a phenyl group substituted by a bromine atom, and, in particular, a 3-bromophenyl or 4-bromophenyl group, whilst $R^2$ represents an n-butyl group, or
- $R^1$ represents a phenyl group, whilst $R^2$ represents an anthracenylmethyl group, or
- $R^1$ represents a benzofuryl group, and, in particular, a 2-benzofuryl group, whilst $R^2$ represents an anthracenylmethyl group, or
- $R^1$ represents a phenyl group, whilst $R^2$ represents an n-butyl group, or
- $R^1$ represents a pyridyl group, whilst $R^2$ represents a phenyl group, or
- $R^1$ represents a phenyl group, whilst $R^2$ represents a naphthylmethyl group, or
- $R^1$ represents a phenethyl group, whilst $R^2$ represents an ethyl group, or
- $R^1$ represents a phenyl group substituted by a bromine atom, and, in particular, a 3-bromophenyl or 4-bromophenyl group, whilst $R^2$ represents an methyl group, or
- $R^1$ represents a phenethyl group, whilst $R^2$ represents a hydrogen atom, or
- $R^1$ represents a carbazolylethyl group, whilst $R^2$ represents a hydrogen atom, or
- $R^1$ represents a 1,1-dioxotetrahydrothien-3-yl group, whilst $R^2$ represents a hydrogen atom, or
- $R^1$ represents a phenethyl group substituted by a phenoxy group, and, in particular, a 4-phenoxyphenethyl group, whilst $R^2$ represents a hydrogen atom.

When they are not commercially available, azaboronates with the general formula (I) may be synthesised by reaction between a bis(hydroxyalkyl)amine corresponding to general formula (II) below:

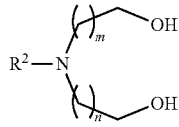

(II)

in which $R^2$, m, and n have the same meaning as above;
and a boronated compound corresponding to general formula (III) below:

(III)

in which $R^2$ has the same meaning as above, whilst Y represents an atom or a group suited to react with a hydroxyl group to form an ether group. Such an atom or group is, e.g., a halogen atom, a hydroxyl group, or an alkoxy group.

If the boronated compound with general formula (III) is a boronic acid (Y=OH), the reaction between this compound and the bis(hydroxylalkyl)amine with general formula (II) is advantageously carried out in the presence of a dehydrating agent such as a molecular sieve, anhydrous sodium sulphate or anhydrous magnesium sulphate, or in a specific Dean-Stark-type device.

If the bis(hydroxyalkyl)amine with general formula (II) is not itself commercially available, it may be obtained by reacting a bis(hydroxyalkyl)amine corresponding to general formula (IV) below:

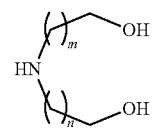

(IV)

in which m and n have the same meaning as above;
with a compound with the general formula $R^2$—X in which X represents a leaving atom such as a halogen atom, or a leaving group such as a mesylate or tosylate group.

According to the invention, the azaboronate with general formula (I) is preferably present in the sensor in the form of a thin film covering one or both surfaces of a substrate properly chosen based on the physical property, the variations in which are to be measured by the sensor.

In one variant, the azaboronate with general formula (I) may also be present in the sensor in the form of a pure object, e.g., a cylinder with a certain porosity, so as to make accessible all molecules of the azaboronate to the peroxides.

When the azaboronate with general formula (I) is in the form of a thin film, the film preferably has a thickness of 10 angströms to 100 micrometers.

Such a film may be obtained, in particular, by spray deposition, spin coating, drop deposition, inkjet deposition, or sublimation deposition; all of these deposition techniques being well known to persons skilled in the art.

The substrate, as well as the sensor's measuring system, are chosen based on the physical property of the azaboronate with general formula (I), the variations induced by the presence of peroxides in which are capable of being measured by the sensor.

Here, the mass variations of the azaboronates with general formula (I) and the fluorescence variations of the azaboronates, when they have fluorescent properties, were found particularly worthwhile to measure.

Thus, the sensor is preferably a gravimetric sensor or a fluorescence sensor.

Examples of gravimetric sensors include quartz microbalance sensors, surface acoustic wave (SAW) sensors, such as Love wave and Lamb wave sensors, as well as microcantilevers.

Amongst the gravimetric sensors, quartz microbalance sensors are particularly preferred. This type of sensor, the operating principle of which was described by J. A. O. Sanchez-Pedrono et al. in *Anal. Chem. Acta*, vol. 182, 1986, 285, comprises, schematically, a piezoelectric substrate (or resonator), generally a quartz crystal covered on both surfaces by a metallic layer, e.g., gold or platinum, serving as an electrode. With the sensitive material covering one or both surfaces of the substrate, any mass variation of the material translates into a variation in the vibration frequency of the sensor.

When the sensor is a fluorescence sensor, the azaboronate with general formula (I) necessarily comprises at least one fluorescent group, and this fluorescent group is bonded to the nitrogen atom of the azaboronate, i.e., it is represented by $R^2$.

According to the invention, it is also possible to use an azaboronate with general formula (I) as the sensitive material in sensors designed to measure variations of a physical property other than mass and fluorescence, e.g., optical sensors based on the measurement of absorbency variations in the visible UV spectrum or wavelength in the infrared spectrum.

Furthermore, it is also possible to combine in a single device or "multisensor" various elementary sensors comprising sensitive materials different to one another or equipped with substrates and measuring systems different to one another, e.g., one or more gravimetric sensors and/or one or more fluorescence sensors; it is essential for one or more of these sensors to comprise an azaboronate with general formula (I).

According to the invention, peroxides to be detected by the sensor are preferably peroxides, including at least one of the two oxygen atoms of the group or one of the —O—O— groups that they include is bonded to a hydrogen atom, by which this oxygen atom forms a hydroxyl group with the hydrogen atom.

Peroxides corresponding to this criterion are, in particular, hydrogen peroxide, hydroperoxides, e.g., t-butyl hydroperoxide, α-cumyl hydroperoxide and 1-phenethyl peroxide, and ketone peroxides, e.g., methylethylketone peroxide, acetylketone peroxide, or cyclohexanone peroxide, whereby hydrogen peroxide is particularly preferred.

Amongst the azaboronates corresponding to general formula (I), some are known and even commercially available, whilst others appear never to have been described in the literature.

The invention thus further concerns an azaboronate corresponding to general formula (I) above, in which m and n are 1, and:

$R^1$ represents a phenyl group, whilst $R^2$ represents an ethyl group, or $R^1$ represents a phenyl group, whilst $R^2$ represents an anthracenyl-methyl group, or $R^1$ represents a benzofuryl group, and, in particular, a 2-benzofuryl group, whilst $R^2$ represents an anthracenylmethyl group, or $R^1$ represents a phenyl group, whilst $R^2$ represents a naphthylmethyl group, or $R^1$ represents a phenethyl group, whilst $R^2$ represents an ethyl group.

The invention further concerns a sensor comprising at least one azaboronate as defined above as a sensitive material.

There, too, the specificities of this sensor are the same as those listed above in relation to the use of an azaboronate with general formula (I) as a sensitive material in a sensor to detect the presence of a peroxide in a gaseous environment.

Other characteristics and benefits of the invention will be more clearly understood from the detailed description below, concerning examples of synthesis of azaboronates that are useful according to the invention, use of these azaboronates as sensitive materials in sensors, and proof of the properties of the sensors thus obtained.

Of course, these examples are provided for illustration of the subject-matter of the invention only, and in no way constitute a limitation of that subject-matter.

DETAILED DESCRIPTION OF SPECIFIC EMBODIMENTS

EXAMPLE 1

Figure 1:
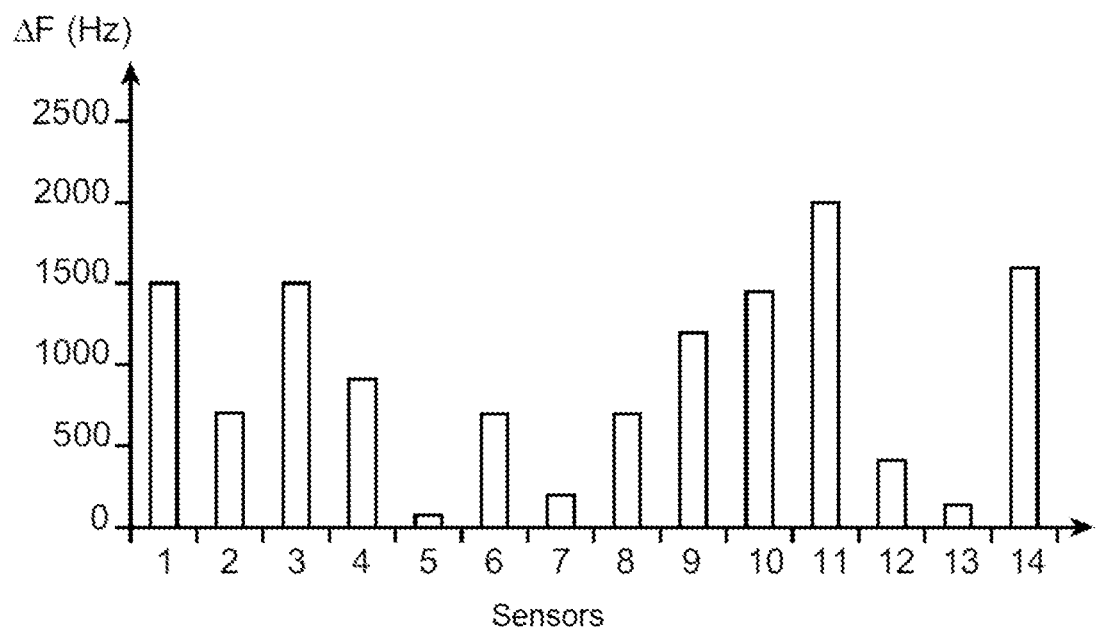
FIG. 1 shows the variations of the vibration frequency of the quartz of fourteen quartz microbalance sensors, each comprising a thin film of an azaboronate useful according to the invention, such as those obtained after 1 minute of exposure to hydrogen peroxide vapours.

Synthesis of the Azaboronates Useful According to the Invention

This example concerns the synthesis of various azaboronates corresponding to general formula (I).

1.1. Synthesis of the Azaboronate with General Formula (I) in which m=n=1, $R^1$=Phenyl, and $R^2$=Ethyl:

In a Dean-Stark assembly, 135 mg (1 mmol) of phenylboronic acid (Aldrich, reference P20009), 112 mg (1 mmol) of N-ethyldiethanolamine (Aldrich, reference 112062), and 30 mL of toluene are introduced.

After 48 hours of reflux, the reaction medium is cooled to room temperature, and the solvent is evaporated.

This yields 175 mg of a yellow solid (i.e., 80% yield), the proton NMR characterisation is provided below.

$^1$H NMR (200 MHz, CDCl$_3$) δ ppm: 1.06 (t, 3H), 2.38 (d, 2H), 2.95 (m, 4H), 4.14 (m, 4H), 7.25 (m, 3H), 7.56 (m, 2H)

1.2. Synthesis of the Azaboronate with General Formula (I) in which m=n=1, $R^1$=Phenyl, and $R^2$=Anthracenylmethyl:

Synthesis of N-anthracenylmethyldiethanolamine:

In a 250 mL flask with a refrigerant, 5 g (22 mmol) of chloromethyl-anthracene (Aldrich, reference 196517), 4.7 g (44 mmol) of diethanolamine (Aldrich, reference D8885), 3.6 g (26 mmol) of potassium carbonate, 100 mg (0.6 mmol) of potassium iodide, and 150 mL of acetonitrile are introduced under argon.

After 5 hours of reflux, the reaction medium is cooled to room temperature, and it is poured into 500 mL of water. The solid thus obtained is filtered and washed with water.

This yields 5,8 g of a yellow solid (i.e., 89% yield), the proton NMR characterisation is provided below.

$^1$H NMR (200 MHz, CDCl$_3$) δ ppm: 2.43 (a, 2H), 2.65 (t, 4H), 3.5 (t, 4H), 4.68 (2H), 7.3-7.6 (m, 4H), 7 (d, 2H), 8.45 (d, 3H)

Synthesis of the azaboronate:

In a Dean-Stark assembly, 118 mg (1 mmol) of phenylboronic acid (Aldrich, reference P20009), 304 mg (1 mmol) of N-anthracenylmethyldiethanolamine, and 30 mL toluene are introduced.

After 24 hours of reflux, the reaction medium is cooled to room temperature, and the solid obtained is filtered.

This yields 298 mg of a yellow powder (i.e., 78% yield), the proton NMR characterisation is provided below.

$^1$H NMR (200 MHz, MeOD) δ ppm: 2.81 (t, 4H), 3.56 (t, 4H), 4.74 (s, 2H), 7.3-7.6 (m, 9H), 8 (d, 2H), 8.5 (s, 1H), 8.6 (d, 2H)

1.3. Synthesis of the Azaboronate with General Formula (I) in which m=n=1, R$^1$=2-benzofuryl, and R$^2$=Anthracenylmethyl:

In a Dean-Stark assembly, 97 mg (6.5 mmol) of 2-benzofurylboronic acid (Aldrich, reference 499943), 201 mg (6.5 mmol) of N-anthracenylmethyldiethanolamine, as obtained in 1.2 above, and 25 mL of toluene are introduced.

After 24 hours of reflux, the reaction medium is cooled to room temperature, and the solid obtained is filtered.

This yields 62 mg of a yellow powder (i.e., 23% yield), the proton NMR characterisation is provided below.

$^1$H NMR (200 MHz, MeOD) δ ppm: 2.95 (s, 4H), 3.62 (t, 4H), 4.9 (d, 2H), 7.16 (m, 2H), 7.5 (m, 6H), 8.02 (d, 2H), 8.54 (S, 1H), 8.59 (s, 2H)

1.4. Synthesis of the Azaboronate with General Formula (I) in which m=n=1, R$^1$=Phenyl, and R$^2$=Naphthylmethyl:

Synthesis of N-naphthylmethyldiethanolamine:

In a 100 mL flask with a refrigerant, 1.76 g (10 mmol) of chloromethylnaphthalene (Aldrich, reference 25170), 2.11 g (20 mmol) of diethanolamine (Aldrich, reference D8885), 1.65 g (12 mmol) of potassium carbonate, 17 mg (0.3 mmol) of potassium iodide, and 35 mL of acetonitrile are introduced under argon.

After 5 hours of reflux, the reaction medium is cooled to room temperature, and it is poured into 500 mL of water. The solid thus obtained is filtered and washed with water.

This yields 2 g of a cream solid (i.e., 82% yield), the proton NMR characterisation is provided below.

$^1$H NMR (200 MHz, CDCl$_3$) δ ppm: 2.71 (t, 4H), 3.29 (s, 4H), 3.51 (t, 4H), 4.1 (s, 2H), 7.5 (m, 4H), 7.8 (, 2H), 8.26 (d, 1H)

Synthesis of the Azaboronate:

In a Dean-Stark assembly, 246 mg (2 mmol) of phenylboronic acid (Aldrich, reference P20009), 500 mg (2 mmol) of N-naphthylmethyldiethanolamine, and 30 mL of toluene are introduced.

After 24 hours of reflux, the reaction medium is cooled to room temperature, and the solid obtained is filtered.

This yields 280 mg of a white powder (i.e., 42% yield), the proton NMR characterisation is provided below.

$^1$H NMR (200 MHz, CDCl$_3$) δ ppm: 3.1 (s, 4H), 3.95 (s, 2H), 4.25 (t, 4H), 7.5 (m, 8H), 7.84 (m, 6H)

1.5. Synthesis of the Azaboronate with General Formula (I) in which m=n=1, R$^1$=Phenethyl, and R$^2$=Methyl:

In a Dean-Stark assembly, 135 mg (2 mmol) of phenethylboronic acid (Aldrich, reference 588423), 122 mg (2 mmol) of N-ethyldiethanolamine (Aldrich, reference 112062), and 30 mL of toluene are introduced.

After 24 hours of reflux, the reaction environment is cooled to room temperature, and the solvent is evaporated.

This yields 392 mg of a yellow solid (i.e., 79% yield), the proton NMR characterisation is provided below.

$^1$H NMR (200 MHz, CDCl$_3$) δ ppm: 0.72 (m, 2H), 1.23 (t, 3H), 2.69 (m, 2H), 2.88 (m, 6H), 3.94 (m, 4H), 7.14 (m, 5H)

EXAMPLE 2

Gravimetric Detection Tests

The suitability of azaboronates with general formula (I) to act as sensitive materials in gravimetric sensors for the detection of the presence of peroxides in a gaseous environment is verified by a series of tests using:

quartz microbalance sensors, comprising an AT-cut quartz with a vibration frequency of 9 MHz, equipped with two circular measurement electrodes in gold (AMETEK PRECISION INSTRUMENTS, model QA9RA-50) as gravimetric sensors; and azaboronates 1 to 14 listed in table 1 below, as sensitive materials; and hydrogen peroxide as a peroxide.

TABLE 1

| Azaboronate with general formula (I) | m | n | R$^1$ | R$^2$ |
|---|---|---|---|---|
| 1  | 1 | 1 | phenyl | ethyl |
| 2  | 1 | 1 | 3-bromophenyl | n-butyl |
| 3  | 1 | 1 | 4-bromophenyl | n-butyl |
| 4  | 1 | 1 | phenyl | anthracenylmethyl |
| 5  | 1 | 1 | 2-benzofuryl | anthracenylmethyl |
| 6  | 1 | 1 | phenyl | n-butyl |
| 7  | 1 | 1 | pyridyl | phenyl |
| 8  | 1 | 1 | phenyl | naphthylmethyl |
| 9  | 1 | 1 | phenethyl | ethyl |
| 10 | 1 | 1 | 3-bromophenyl | methyl |
| 11 | 1 | 1 | phenethyl | H |
| 12 | 1 | 1 | carbazolylethyl | H |
| 13 | 1 | 1 | 1,1-dioxotetrahydrothien-3-yl | H |
| 14 | 1 | 1 | 4-phenoxyphenethyl | H |

Azaboronates 1, 4, 5, 8, and 9 correspond to the 5 azaboronates, the synthesis of which is described in example 1 above, whilst azaboronates 2, 3, 6, 7, and 10 to 14 are the compounds available, for the first four, from Aldrich under references 680486, 680494, 680478, and 647284, and, for the last five, from Alfa Aesar under references L17796, L19706, L19575, H31355, and H31401.

For the requirements of the tests, a thin film of one of azaboronates 1 to 14 is deposited on one of the surfaces of each quartz. These depositions are carried out by spin coating, or by pulverisation from solutions containing 4 to 7 mg/mL of the azaboronate in the chloroform.

The formation of the films results in a loss in the vibration frequency of the quartz of the sensors of 3 to 7 kHz.

The sensors are then exposed to ambient air for 30 minutes, then to hydrogen peroxide, at a concentration close to the vapour pressure of the peroxide, or approximately 1500 ppm, in ambient air, for 10 minutes, and again in ambient air for 20 minutes.

The sensitivity of the sensors to hydrogen peroxide is determined by determining, for each of them, the variation (ΔF) in the vibration frequency of the quartz obtained after 1 minute exposure to hydrogen peroxide; this variation is determined as follows:

ΔF=average of the frequencies measured before exposure to H$_2$O$_2$–vibration frequency at exposure time $t_{1\ min}$ to H$_2$O$_2$.

The results are shown in FIG. 1 in the form of a graphic indicating the ΔF values, expressed in hertz (Hz), such as those obtained by each of the sensors. In this drawing, the sensors are numbered 1 to 14, and have the same number as that of the azaboronate covering their quartz.

This drawing shows that all of the sensors tested reacted to the presence of the hydrogen peroxide from the first minute of exposure to that peroxide, as a drop in the vibration frequency of the quartz, more or less pronounced, but still significant, is observed in each of them. In this regard, it is in fact worth noting that, in the field of quartz microbalance sensors, a variation in the vibration frequency of the quartz of a sensor is considered significant, and thus can be used, when it is more than three times the background noise of the sensor, i.e., approximately 10 Hz in this case. As can be seen in FIG. 1, the drop in the vibration frequency of the quartz of the 14 sensors tested is much greater than this that minimum value.

Figure 2:
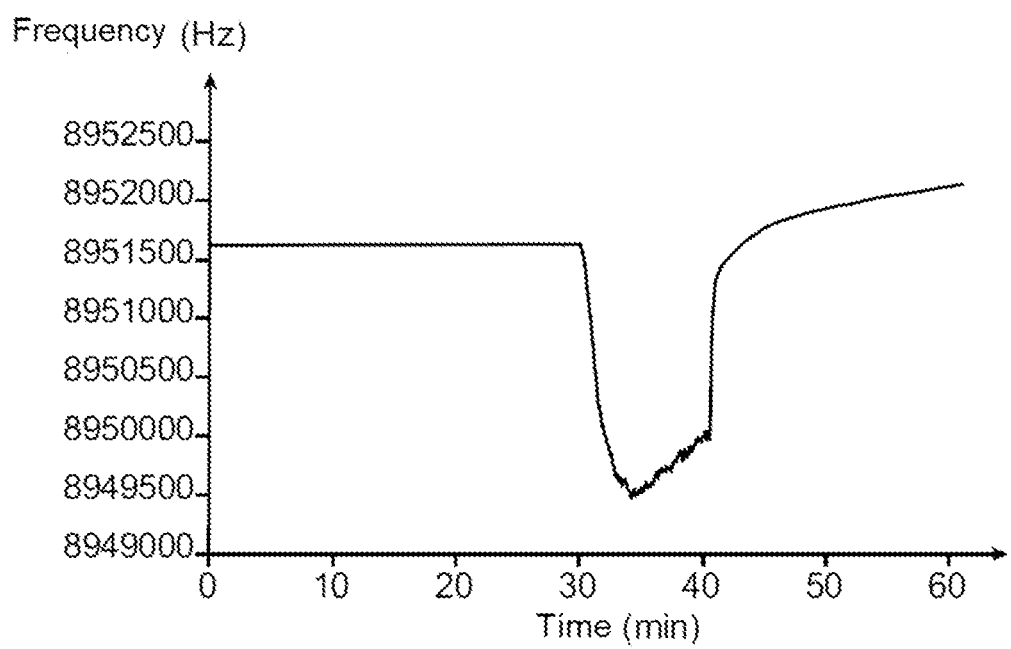
FIGS. 2, 3, and 4 show the development of the vibration frequency of the quartz of three quartz microbalance sensors, each comprising a thin film of an azaboronate useful according to the invention, such as one obtained after these sensors have been successively exposed to ambient air for 30 minutes, to hydrogen peroxide vapours for 10 minutes, and to ambient air for 20 minutes.
Figure 3:
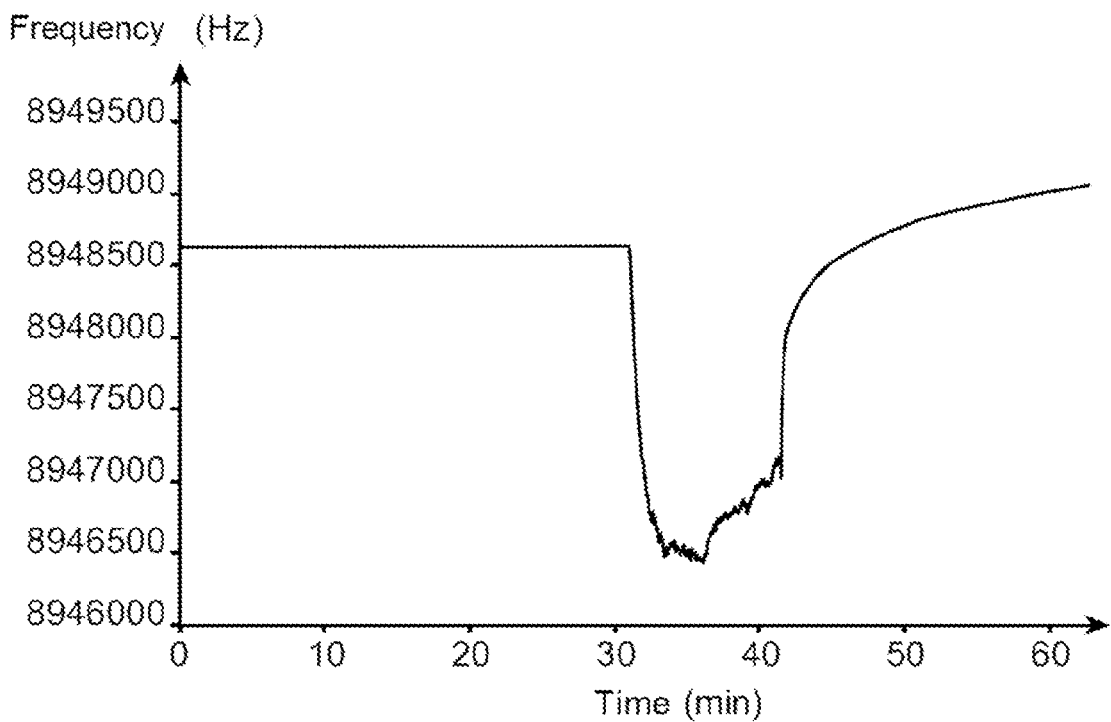
Figure 4:
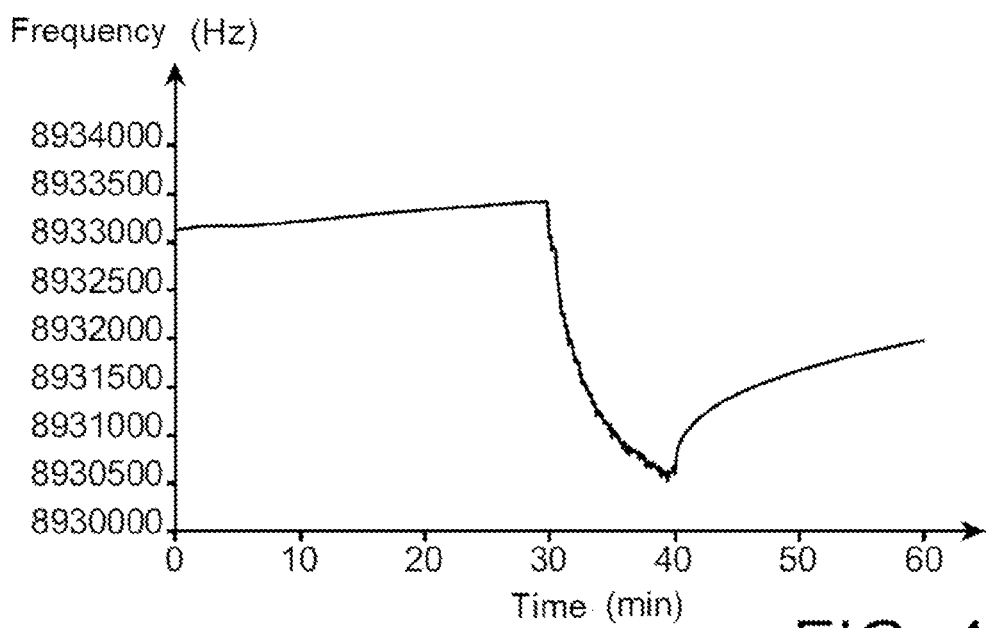

Additionally, FIGS. 2, 3, and 4 show the development of the vibration frequency of the quartz of the sensors respectively comprising 2, 3, and 4 as sensitive materials, as observed over the entire duration of the exposures of these sensors to ambient air and hydrogen peroxide, in the form of a curve showing the quartz vibration frequency values, expressed in Hz, as a function of time, expressed in minutes.

These figures confirm that the drop in the quartz vibration frequency of the sensors is in fact induced by the presence of hydrogen peroxide, and begins once the sensors have been placed in contact with the peroxide.

This drop then continues, reaching the value of 2100 Hz in the case of the sensors with azaboronates 2 and 3 as sensitive materials, and that of 3000 Hz for the sensor with azaboronate 4 as a sensitive material.

This drop is reversible, as the return of the sensors to contact with ambient air results in an increase in the quartz vibration frequency, rapid in the case of the sensors with azaboronates 2 and 3 as sensitive materials, slower in the case of the sensor with azaboronate 4 as a sensitive material.

EXAMPLE 3

Fluorescence Detection Tests

To verify the suitability of the azaboronates with general formula (I), in which $R^2$ represents a fluorescent group, to serve as sensitive materials in fluorescence sensors for the detection of the presence of peroxides, and, in particular hydrogen peroxide, in a gaseous environment, a first test is carried out using the azaboronates respectively numbered 4 and 5 in table 1 above.

For the requirements of these tests, a thin film of one of these azaboronates is deposited on one of the surfaces of two glass microscope slide-type substrates (75×25 mm×1 mm, Heathrow Scientific), a thin film of one of these azaboronate by spin coating from a solution containing 5 mg/mL of azaboronate 4 in chloroform.

These sensors are then exposed to ambient air for 30 minutes, then to hydrogen peroxide, at a concentration close to the vapour pressure of the peroxide, or approximately 1500 ppm, in ambient air, for 10 minutes, and again in ambient air for 20 minutes.

Figure 5:
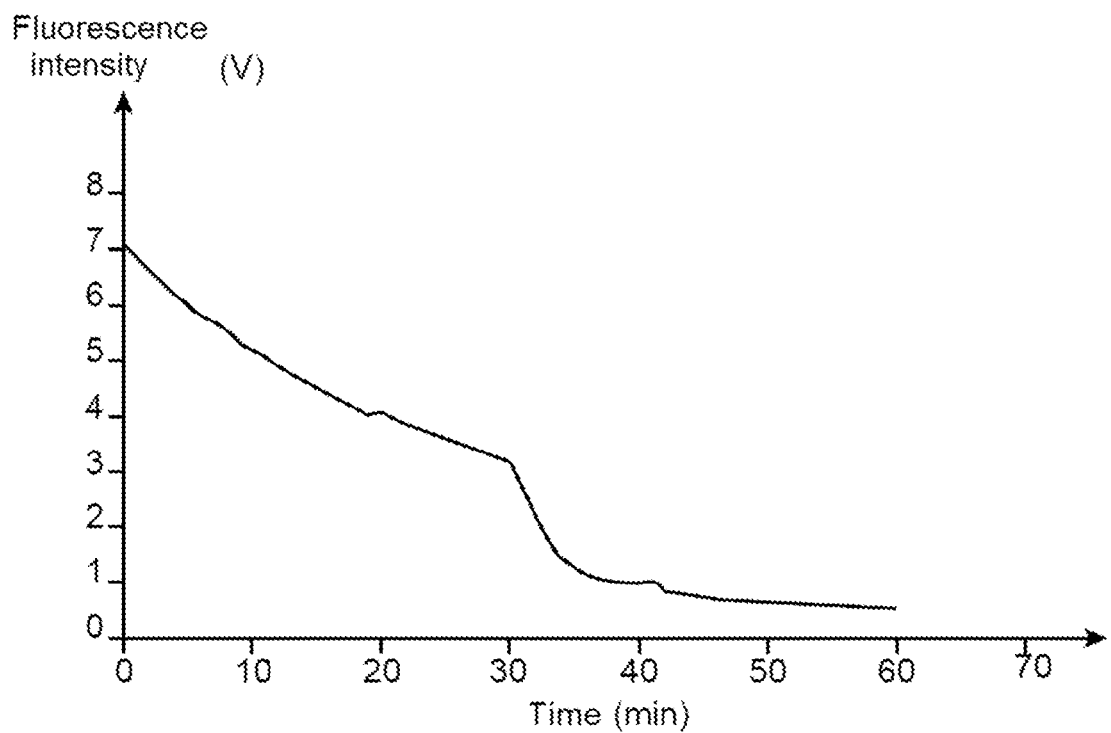
FIGS. 5 and 6 show the development of the fluorescent signal intensity emitted by two fluorescence sensors, each comprising a thin film of an azaboronate useful according to the invention, such as one obtained after these sensors have been successively exposed to ambient air for 30 minutes, to hydrogen peroxide vapours for 10 minutes, and to ambient air for 20 minutes.
Figure 6:
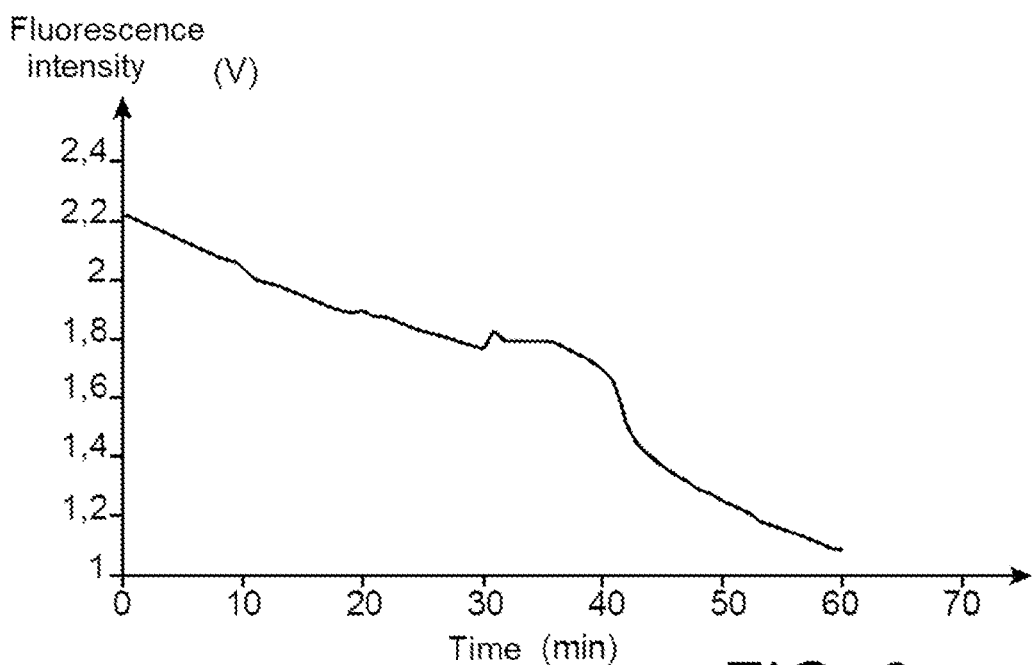

FIGS. 5 and 6 show the development of the fluorescent signal emitted by these sensors during these exposures in the form of curves representing the intensity of the signal, expressed in volts, as a function of time, expressed in minutes ($\lambda_{excitation}$: 300-380 nm; $\lambda_{emission}$: >420 nm).

FIG. 5 corresponds to the sensor with azaboronate 4 as the sensitive material, whilst FIG. 6 corresponds to the sensor with azaboronate 5 as the sensitive material.

These figures show that both sensors reacted to the presence of the hydrogen peroxide from the time they were placed in contact with the peroxide, but that they reacted differently, as a drop in the intensity of the fluorescent signal emitted by the sensor with azaboronate 4 as the sensitive material was observed, whilst, on the contrary, an increase in the intensity of the fluorescent signal emitted by the sensor with azaboronate 5 as a sensitive material was observed.

In both cases, the modification in the intensity of the fluorescent signal is sufficiently pronounced to be exploitable.

A second test is carried out:
  by depositing on one of the surfaces of a quartz substrate a thin film of the azaboronate numbered 8 on table 1 above by spin coating from a solution containing 5 mg/mL of the azaboronate in the chloroform;
  by measuring the fluorescence emission spectrum ($\lambda_{excitation}$: 287 nm) of the sensor thus obtained (t0);
  by exposing this sensor to hydrogen peroxide at a concentration close to the vapour pressure of the peroxide, i.e., approximately 1500 ppm, and ambient air, for 10 minutes; and
  by re-measuring the fluorescence emission spectrum of the sensor following this exposure (t10).

Figure 7:
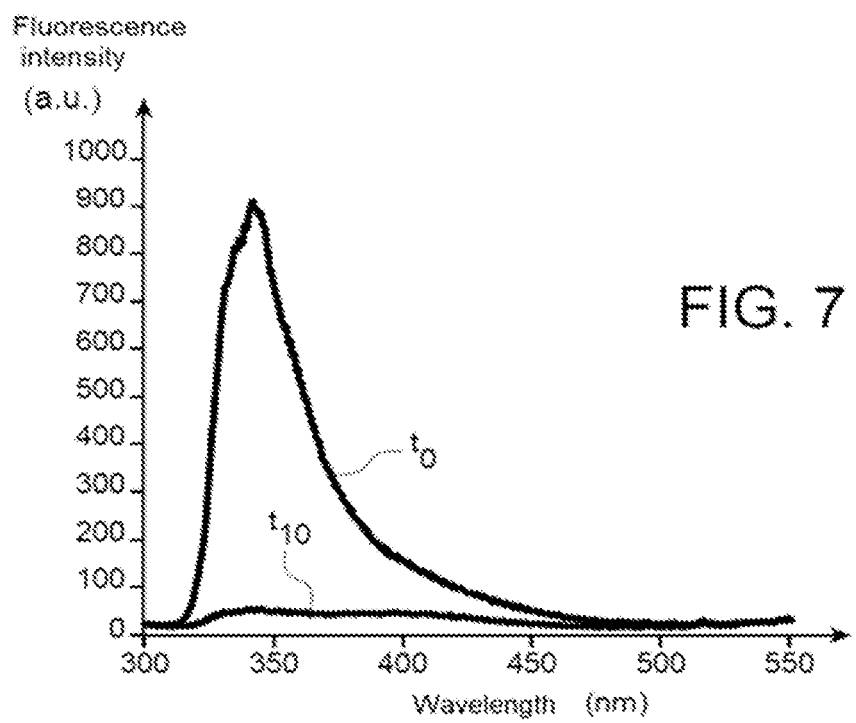
FIG. 7 shows the fluorescence emission spectra of a thin film of an azaboronate useful according to the invention, such as those obtained before exposing the thin film to hydrogen peroxide vapours (t0) and after exposing the thin film to hydrogen peroxide vapours for 10 minutes.

FIG. 7 shows the fluorescence emission spectra of the sensor, as obtained at t0 and t10, respectively.

As shown in this figure, the sensor reacted very strongly to the presence of the hydrogen peroxide, as its being placed in contact with the peroxide resulted in extinguishment of the fluorescence.

A third test is carried out:
  by depositing on one of the surfaces of a quartz substrate a thin film of the azaboronate numbered 4 on table 1 above by spin coating from a solution containing 5 mg/mL of the azaboronate in the chloroform;
  by exposing the sensor thus obtained to humid air for 30 minutes, then to triacetone triperoxide (TATP), at a concentration on the order of 20 ppm, in humid air, for 10 minutes, then again in humid air for 10 minutes, then again in humid air for 20 minutes, then again in TATP, also at a concentration on the order of 20 ppm, in humid air for 10 minutes, and lastly in humid air for 30 minutes; and
  by monitoring the development of the intensity of the fluorescent signal emitted by the sensor during these exposures.

Figure 8:
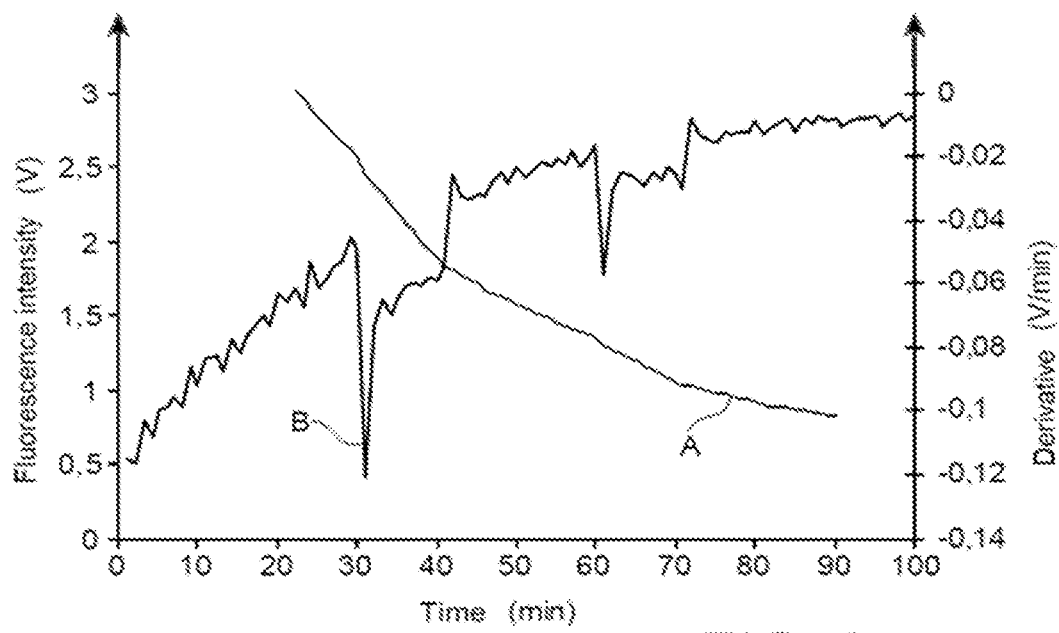
FIG. 8 represents the development of the fluorescent signal intensity (curve A) emitted by a fluorescence sensor comprising a thin film of an azaboronate useful according to the invention, such as one obtained when the sensor is successively exposed to humid air for 30 minutes, to triacetone triperoxide (TATP) vapours for 10 minutes, humid air for 20 min, TATP vapours for 10 minutes, and to humid air for 30 minutes; on this drawing, the derivative of the fluorescence intensity of the signal as a function of time is also shown (curve B).

This development is shown in FIG. 8, in the form of a curve (curve A), representing the intensity of the fluorescent signal, expressed in volts, as a function of time, expressed in minutes ($\lambda_{excitation}$: 300-380 nm; $\lambda_{emission}$: >420 nm). FIG. 8 also shows the derivative of the intensity of the fluorescent signal as a function of time (curve B).

This figure shows that the sensor did in fact react to the presence of TATP from the moment it was placed in contact with this peroxide. The effects of the presence of TATP on the fluorescence signal emitted by the sensor are particularly visible in curve B of this figure.

The invention claimed is:

1. A method for detecting a presence of a peroxide in a gaseous medium, comprising:
  contacting the gaseous medium with a gravimetric sensor comprising a sensitive material, the sensitive material comprising an azaboronate having a mass which is modified on contact with the peroxide, the azaboronate corresponding to general formula (I) below:

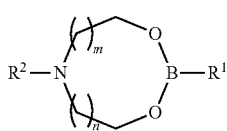

in which:

m and n independently represent a whole number from 1 to 10;

$R^1$ is an aliphatic, cyclic, or partially aliphatic and partially cyclic hydrocarbon group, saturated or unsaturated, comprising 1 to 30 carbon atoms and possibly one or more heteroatoms and/or one or more substituents;

$R^2$ is a hydrogen atom or an aliphatic, cyclic, or partially aliphatic and partially cyclic hydrocarbon group, saturated or unsaturated, comprising 1 to 30 carbon atoms and optionally one or more heteroatoms and/or one or more substituents;

the sensor providing a first response when the peroxide is not present in the gaseous medium and providing a second response when the peroxide is present in the gaseous medium, the second response being different from the first response and corresponding to a modification of the mass of the azaboronate on contact with the peroxide;

measuring a change in the response of the sensor and correlating the change of the response to the presence of the peroxide in the gaseous medium.

2. The method of claim 1, in which $R^1$ or $R^2$ is a hydrocarbon group chosen from linear or branched alkyl groups, linear or branched alkenyl groups, linear or branched alkynyl groups, cycloalkyl groups, cycloalkenyl groups, cycloalkynyl groups, heterocycloalkyl groups, aryl groups, heteroaryl groups, arylalkyl groups, heteroarylalkyl groups and groups derived therefrom by one or more substitutions, the substituent(s) being chosen from halogen atoms and groups comprising one or more atoms chosen from oxygen, nitrogen, sulphur, and halogen, and a number of carbon atoms from 0 to 10.

3. The method of claim 2, in which $R^1$ is an alkyl group comprising 1 to 6 carbon atoms, a heterocycloalkyl group comprising 1 to 3 cycles with 5 or 6 members each, an aryl or heteroaryl group comprising 1 to 3 cycles with 5 or 6 members each, an arylalkyl or heteroarylalkyl group in which the alkyl radical comprises 1 to 6 carbon atoms, and in which the aryl or heteroaryl radical comprises 1 to 3 cycles with 5 or 6 members each, or a group derived therefrom by one or more substitutions, the substituent(s) being chosen from halogen atoms and groups comprising one or more atoms chosen from oxygen, nitrogen, sulphur, and halogen, and a number of carbon atoms from 0 to 10.

4. The method of claim 3, in which $R^1$ is a phenyl group, a phenyl group substituted by one or more halogen atoms, a benzofuryl group, a phenethyl group, a phenethyl group substituted by a phenoxy group, a pyridyl group, a carbazolylethyl group, a tetrahydrothienyl group, or a tetrahydrothienyl group in which the sulphur atom is bonded to two oxygen atoms.

5. The method of claim 2, in which $R^2$ is a hydrogen atom or an alkyl group comprising 1 to 6 carbon atoms, a heterocycloalkyl group comprising 1 to 3 cycles with 5 or 6 members each, an aryl or heteroaryl group comprising 1 to 3 cycles with 5 or 6 members each, an arylalkyl or heteroarylalkyl group in which the alkyl radical comprises 1 to 6 carbon atoms, and in which the aryl or heteroaryl radical comprises 1 to 3 cycles with 5 or 6 members each, or a group derived therefrom by one or more substitutions, the substituent(s) being chosen from halogen atoms and groups comprising one or more atoms chosen from oxygen, nitrogen, sulphur, and halogen, and a number of carbon atoms from 0 to 10.

6. The method of claim 5, in which $R^2$ is a hydrogen atom, an alkyl group comprising 1 to 4 carbon atoms, a phenyl group, a naphthylmethyl group, or an anthracenylmethyl group.

7. The method of claim 1, in which one of $R^1$ and $R^2$ is a fluorescent group.

8. The method of claim 1, in which m and n are, independently, 1 or 2.

9. The method of claim 1, in which the azaboronate corresponds to general formula (I), in which m and n are 1, and in which:

$R^1$ is a phenyl group and $R^2$ is an ethyl group, or $R^1$ is a phenyl group substituted by a bromine atom and $R^2$ is an n-butyl group, or $R^1$ is a phenyl group and $R^2$ is an anthracenylmethyl group, or $R^1$ is a benzofuryl group and $R^2$ is an anthracenylmethyl group, or $R^1$ is a phenyl group and $R^2$ is an n-butyl group, or $R^1$ is a pyridyl group and $R^2$ is a phenyl group, or $R^1$ is a phenyl group and $R^2$ is a naphthylmethyl group, or $R^1$ is a phenethyl group and $R^2$ is an ethyl group, or $R^1$ is a phenyl group substituted by a bromine atom and $R^2$ is a methyl group, or $R^1$ is a phenethyl group and $R^2$ is a hydrogen atom, or $R^1$ is a carbazolylethyl group and $R^2$ is a hydrogen atom, or $R^1$ is a 1,1-dioxotetrahydrothien-3-yl group and $R^2$ is a hydrogen atom, or $R^1$ is a phenethyl group substituted by a phenoxy group and $R^2$ is a hydrogen atom.

10. The method of claim 1, in which the sensor comprises a substrate having two faces and the sensitive material is in the form of a thin film covering one or both surfaces of the substrate.

11. The method of claim 1, in which the gravimetric sensor is a quartz balance sensor.

12. The method of claim 1, in which the peroxide is hydrogen peroxide, a hydroperoxide or a ketone peroxide.

13. The method of claim 12, in which the peroxide is hydrogen peroxide.

14. An azaboronate corresponding to general formula (I) below:

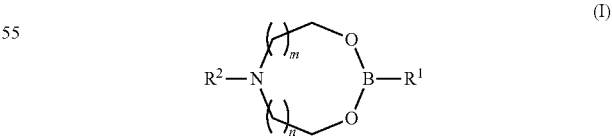

in which m and n equal 1 and:

$R^1$ is a phenyl group and $R^2$ is an anthracenylmethyl group, or $R^1$ is a benzofuryl group and $R^2$ is an anthracenylmethyl group, or $R^1$ is a phenyl group and $R^2$ is a naphthylmethyl group, or $R^1$ is a phenethyl group and $R^2$ is an ethyl group.

15. A gravimetric sensor comprising:
a substrate having two faces;
a sensitive material in the form of a thin film covering one or both faces of the substrate, the sensitive material comprising an azaboronate of claim 14; and
a system for measuring a modification of the azaboronate.

16. The sensor of claim 15 wherein the gravimetric sensor is a quartz microbalance sensor.

17. The sensor of claim 15, wherein the sensor is capable of detecting hydrogen peroxide.

* * * * *